(12) United States Patent
Tano et al.

(10) Patent No.: US 7,974,699 B2
(45) Date of Patent: Jul. 5, 2011

(54) VISION REGENERATION ASSISTING DEVICE

(75) Inventors: Yasuo Tano, Kobe (JP); Hirokazu Sakaguchi, Minoo (JP); Eiji Yonezawa, Okazaki (JP); Hiroyuki Kanda, Minoo (JP)

(73) Assignee: Nidek Co., Ltd., Gamagori-shi (JP)

( * ) Notice: Subject to any disclaimer, the term of this patent is extended or adjusted under 35 U.S.C. 154(b) by 299 days.

(21) Appl. No.: 11/727,155

(22) Filed: Mar. 23, 2007

(65) Prior Publication Data
US 2007/0225775 A1    Sep. 27, 2007

(30) Foreign Application Priority Data

Mar. 24, 2006   (JP) .................................. 2006-081943

(51) Int. Cl.
*A61N 1/36*    (2006.01)
(52) U.S. Cl. ............................................. 607/54
(58) Field of Classification Search ................. 607/54, 607/141, 116; 623/6.63
See application file for complete search history.

(56) References Cited

U.S. PATENT DOCUMENTS

| | | | |
|---|---|---|---|
| 5,109,844 A | 5/1992 | De Juan, Jr. et al. | |
| 5,944,747 A | 8/1999 | Greenberg et al. | |
| 2002/0010496 A1* | 1/2002 | Greenberg et al. | 607/54 |
| 2004/0102843 A1* | 5/2004 | Yagi | 623/4.1 |
| 2004/0172100 A1* | 9/2004 | Humayun et al. | 607/54 |
| 2006/0058857 A1 | 3/2006 | Tano et al. | |
| 2007/0027502 A1 | 2/2007 | Tano et al. | |
| 2007/0038266 A1* | 2/2007 | Greenberg et al. | 607/54 |
| 2007/0055336 A1* | 3/2007 | Greenberg et al. | 607/141 |

FOREIGN PATENT DOCUMENTS

WO    WO 2004/049986 A1    6/2004

OTHER PUBLICATIONS

Montgomery, Ted M., "The Optic Nerve", Anatomy, Physiology and Pathology of the Human Eye, c.1998-2010.*

* cited by examiner

*Primary Examiner* — Carl H Layno
*Assistant Examiner* — Paula J Stice
(74) *Attorney, Agent, or Firm* — Oliff & Berridge, PLC

(57) ABSTRACT

A vision regeneration assisting device for regenerating vision of a patient, comprising: a plurality of electrodes which are stuck and placed into an optic disc of the patient; a storage unit which stores a generation position of a phosphene specific to the patient in association with the first output conditions for the stimulation signal that has caused to generate the phosphene, the storage unit storing various first output conditions for the stimulation signals and the generation positions of the phosphenes caused by the stimulation signals based on the various first output conditions in association with each other; a processor which sets second output conditions for the stimulation signal based on image data obtained by an external photography unit and the generation positions of the phosphenes stored in the storage unit, and converts the obtained image data into data for the stimulation signal based on the set second output conditions.

2 Claims, 7 Drawing Sheets

CURRENT—PULSE-WIDTH :

40 Hz
★ 50 μA-350μs  ×2
● 70 μA-250μs  ×7
◆ 100 μA-180μs  ×1
✚ 150 μA-120 μs  ×2

20 Hz
✧ 30 μA-580 μs  ×1
○ 70 μA-250 μs  ×1

VISION REGENERATION ASSISTING DEVICE

BACKGROUND OF THE INVENTION

1. Field of the Invention

The present invention relates to a vision regeneration assisting device for regenerating (reviving) vision.

2. Description of the Related Art

In a human eye, when the retina is irradiated with light, an optical signal is converted into an electrical signal at (by) the visual cell, and then, this electrical signal is obtained as a pulse signal at (by) the retinal ganglion cell, and then, this pulse signal is transmitted to the brain. However, if, for example, the visual cells decrease, or the visual cells become extinct due to pigmentary retinal degeneration or age-related macular degeneration, the optical signal cannot be converted into the electrical signal, and then, vision (a visual sense) cannot be obtained. In order to solve this problem, in recent years, a variety of devices have been proposed for regenerating vision of a patient who is losing eyesight. The Applicant also proposes a device for applying electrical stimulation through the optic disc of a patient who is losing eyesight so as to regenerate the patient's vision (refer to US 2006/0058857A WO/2004/049986 A).

SUMMARY OF THE INVENTION

The present invention addresses a technical problem of providing a vision regeneration assisting device for applying electrical stimulation through an optic disc under applying conditions that are suitable for an individual patient so as to regenerate the patient's vision.

In order to solve the technical problem described above, the present invention is characterized by comprising the constituent elements set out below.

(1) A vision regeneration assisting device for regenerating vision of a patient, comprising:

a plurality of electrodes which are stuck and placed into an optic disc of the patient;

a setting unit with which first output conditions for an electrical stimulation pulse signal from at least one of the electrodes are set variably;

a storage unit which stores a generation position of a phosphene specific to the patient in association with the first output conditions for the stimulation signal that has caused to generate the phosphene, the storage unit storing various first output conditions for the stimulation signals and the generation positions of the phosphenes caused by the stimulation signals based on the various first output conditions in association with each other;

a processor which sets second output conditions for the stimulation signal based on image data obtained by an external photography unit and the generation positions of the phosphenes stored in the storage unit, and converts the obtained image data into data for the stimulation signal based on the set second output conditions; and a controller which controls output of the stimulation signal from at least one of the electrodes based on the converted stimulation signal data.

(2) The vision regeneration assisting device according to (1), wherein the processor extracts an optimal generation position among the stored generation positions of the phosphenes based on the obtained image data, and sets the first output conditions associated with the extracted generation position to the second output conditions.

(3) The vision regeneration assisting device according to (1), wherein the output conditions for the stimulation signal include at least two among a current value, a frequency and a pulse width of the stimulation signal.

(4) The vision regeneration assisting device according to (1), wherein the storage unit includes a display unit and an input unit for mapping the generation positions of the phosphenes.

BRIEF DESCRIPTIONS OF THE DRAWINGS

Figure 7:
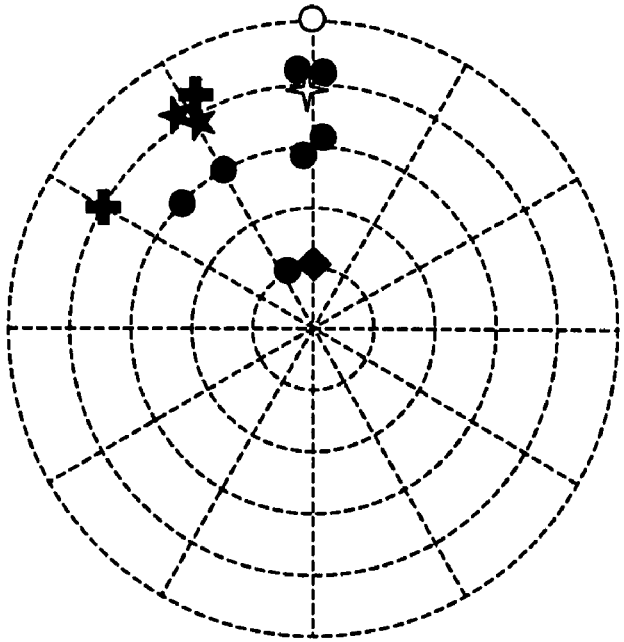
Figure 8:
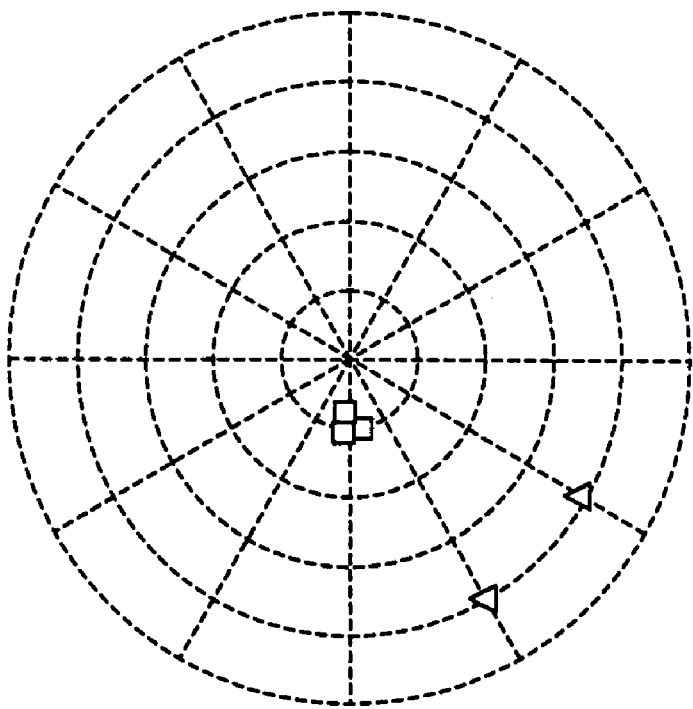

FIG. 7 is a view of a change in generation positions of phosphenes, the change being caused by a difference in output conditions for an electrical stimulation pulse signal from an electrode; and FIG. 8 is a view of a change in generation positions of phosphenes, the chance being caused by a difference in a combination of electrodes that are made to output electrical stimulation pulse signals at the same time.

PREFERRED EMBODIMENTS OF THE INVENTION

Figure 1:
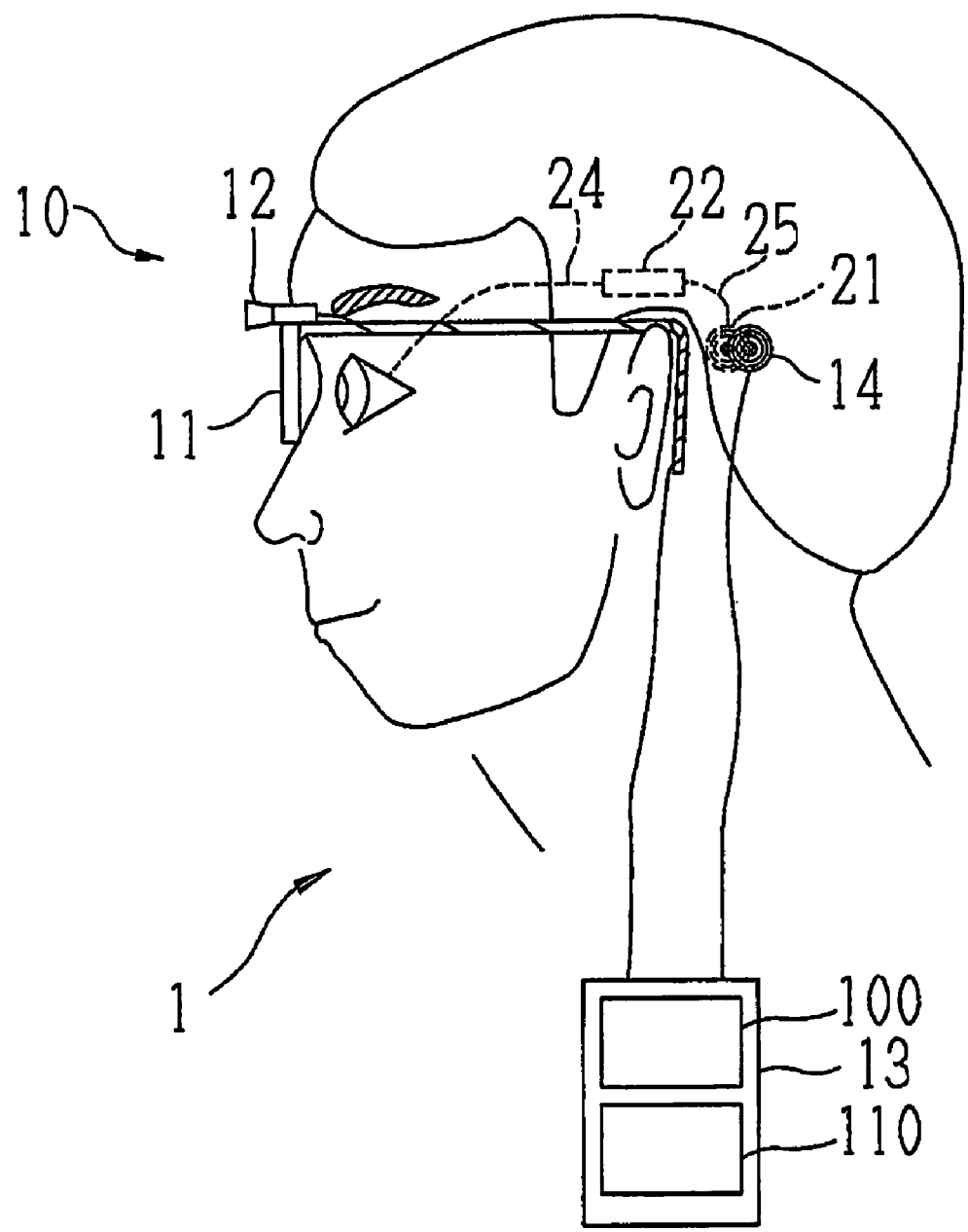
FIG. 1 is a view of a user state of a vision regeneration assisting device according to an embodiment of the present invention.
Figure 2:
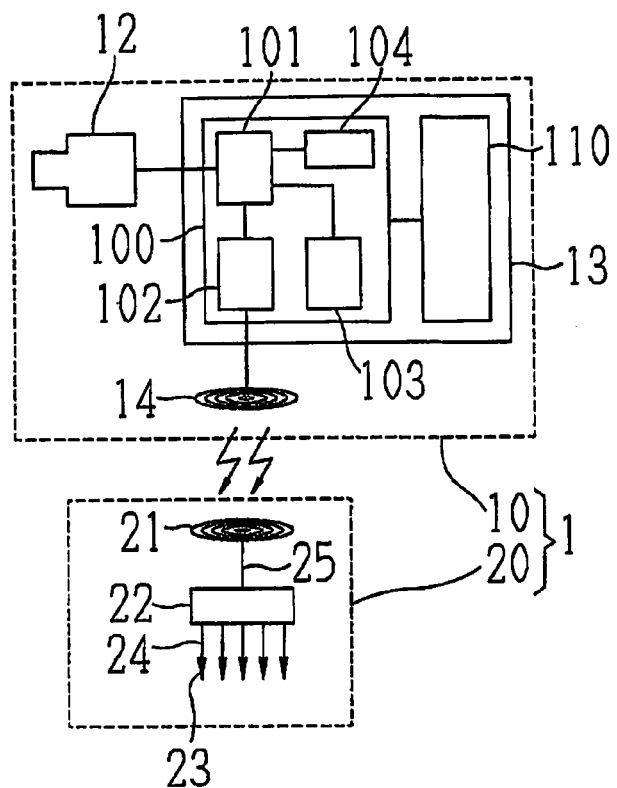
FIG. 2 is a block diagram depicting a schematic construction of the vision regeneration assisting device.

Preferred embodiments of the present invention will be described with reference to the accompanying drawings. FIG. 1 is a view of a vision regeneration assisting device according to an embodiment of the present invention, and FIG. 2 is a block diagram depicting a schematic construction of the vision regeneration assisting device. A vision regeneration assisting device 1 includes an external device 10 and an internal device 20.

The external device 10 includes a visor 11 that a patient wears; a photography unit 12 that consists of equipment such as a CCD camera to be mounted on the visor 11; an external unit 13, and a primary coil (a transmitter unit) 14. The visor 11 is formed in a shape of an eyeglass, and is used by being mounted in front of the patient's eyes. In addition, the photography unit 12 is mounted in front of the visor 11, and then photographs an object to be recognized by the patient.

The external unit 13 includes: a processing unit 100; and a power unit (a battery) 110 for supplying power to the apparatus 1 (the external device 10 and the internal device 20). The processing unit 100 includes: a control section (a controller) 101 that consists of equipment such as a CPU; a signal converter section (a processor) 102 for processing image data from the photography unit 12 to convert the image data into data for an electrical stimulation pulse signal (hereinafter, referred to as a "stimulation signal"); a setting section (a setting unit) 103; and a storage section (a storage unit) 104. The photography unit 12, the signal converter section 102, the setting section 103, and the storage section 104 are connected to the control section 101, respectively. The primary coil 14 is connected to the signal converter section 102.

The setting section 103 has a variety of operating buttons (an input section (an input unit)) and is used to set an output condition for the stimulation signal from an electrode 23 described below (hereinafter, referred to as a "stimulation condition"). In addition, when the stimulation signal is output under the stimulation condition that has been set, the setting section 103 is used to record a generation position and a shape (mainly, a size) of a light perception (a quasi-photesthesia or an intraocular flash) called a phosphene that is not dependent on an optic stimulation (a light stimulus) and is recognized by the patient.

Figure 3:
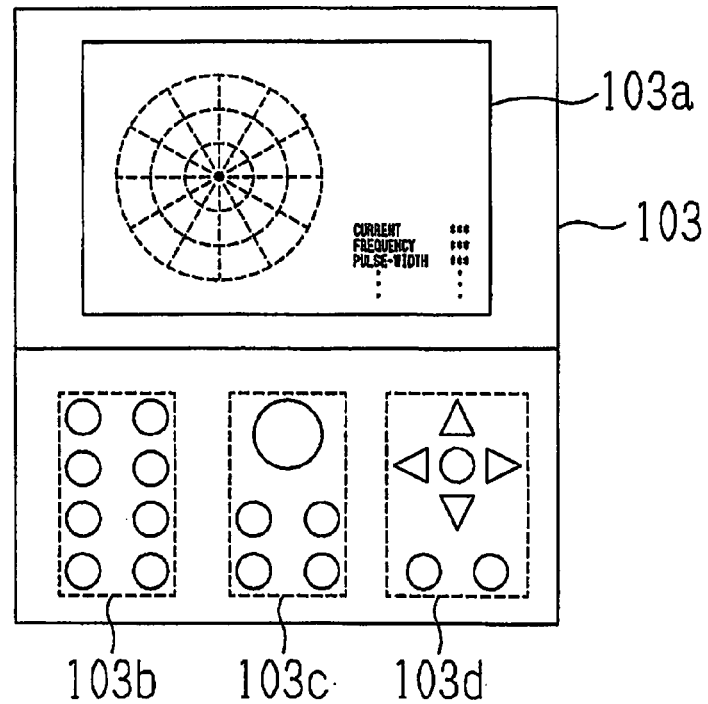
FIG. 3 is a schematic view of a setting section for setting output conditions for an electrical stimulation pulse signal.

FIG. 3 is a schematic view of the setting section 103. A display (a display section (a display unit)) 103a displays the set stimulation conditions, the generation position of the phosphene and the like. An electrode-specifying section 103b has operating buttons (an input section (an input unit)) for specifying the electrode 23 that outputs the stimulation signal. A stimulation condition-setting section 103a has operating buttons (an input section (an input unit)) that include a dial for setting the output conditions for the stimulation signal (stimulation conditions) from the specified electrode 23. A phosphene-recording section 103d has operating buttons (an input section (an input unit)) that include a joystick for recording, by the stimulation signal output from the specified electrode under the set stimulation conditions, the position in the visual field of the patient at which the phosphene has generated.

The storage section 104 stores a plurality of the stimulation conditions set by the setting section 103 and the generation positions of the phosphenes corresponding to the set stimulation conditions in association with each other.

It is preferable that the external unit 13 be of a size such that the unit 13 can be carried by the patient. Moreover, the setting section 103 may be incorporated into the external unit 13 or may be packaged separately.

The primary coil 14 transmits to the internal device 20, as electromagnetic waves, the stimulation signal data converted by the processing unit 100 (the signal converter section 102), and the electric power from the power unit 110. A magnet (not shown) for use in identification of a position relevant to a secondary coil 21 described below is mounted at the center of this primary coil 14.

The internal device 20 includes: a secondary coil (a receiver unit) 21; a processing control section (a processor and a controller) 22; and a plurality of electrodes 23 of which a distal end is formed in a needle shape. The secondary coil 21 and the processing control section 22 are connected to each other through a lead wire 25. Further, the electrodes 23 are connected to the processing control section 22 through lead wires 24, respectively.

The secondary coil 21 receives the electromagnetic waves from the external device 10 (the primary coil 14). A magnet (not shown) for use in identification of a position relevant to the primary coil 14 is mounted at the center of this secondary coil 21.

The processing control section 22 separates the stimulation signal data and the electric power received by the secondary coil 21 from each other; converts the stimulation signal data into the stimulation signal; and then, outputs the stimulation signal to distribute to the electrodes 23.

Each of the electrodes 23 is made of a good biocompatible and corrosion-resistant material that also has electrical conductivity, such as gold or platinum, and is formed in a shape such as a needle shape in such a way that it can be easily stuck into the optic disc. In addition, each of the electrodes 23, at its distal end, is formed in a shape such as an arrowhead shape in such a way that it cannot be easily removed. Further, each of the electrodes 23 is formed in such a way that its diameter is rigid so that it can accordingly be stuck into the optic disc.

With exception of a distal portion of each of the electrodes 23, the internal device 10 is entirely covered with a good biocompatible material that also has an insulation property such as polyimide or polyparaxylilene. In addition, the lead wires 24 are consolidated into a tube 24a made of a good biocompatible and flexible material, such as silicon. Further, a diameter of each of the lead wires 24 need not necessarily be equal to that of each of the electrodes 23, but may rather be determined with due consideration given to levels of rigidity and flexibility.

The internal device 20 is placed (implanted) in advance in the patient's body by a surgical operation. For example, the secondary coil 21 and the processing control section 22, as shown in FIG. 1, are placed (implanted) under the skin of the temporal part of the patient. The primary coil 14 is placed on the skin at a position opposite to that of the secondary coil 21.

Figure 4A:
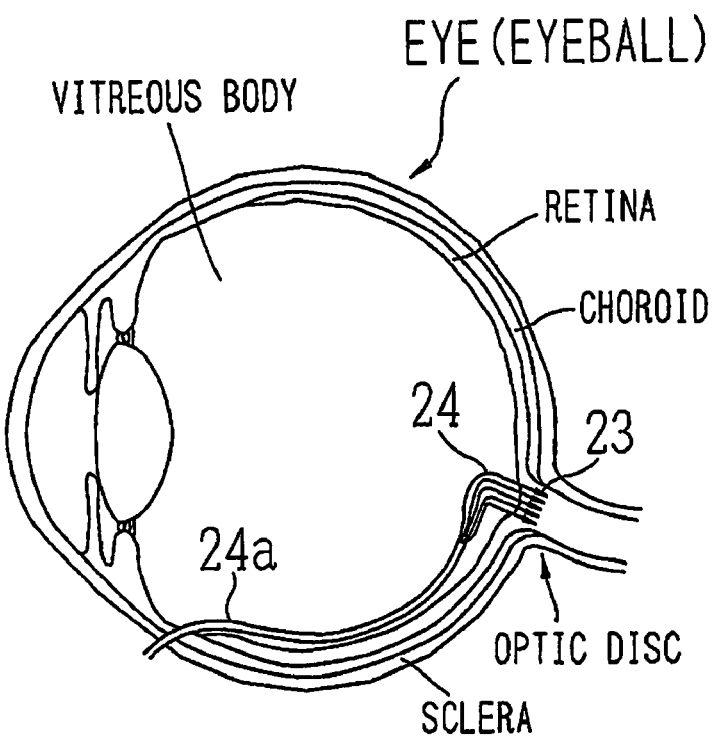
FIG. 4A and FIG. 4B are views of a state in which electrodes are placed.
Figure 4B:
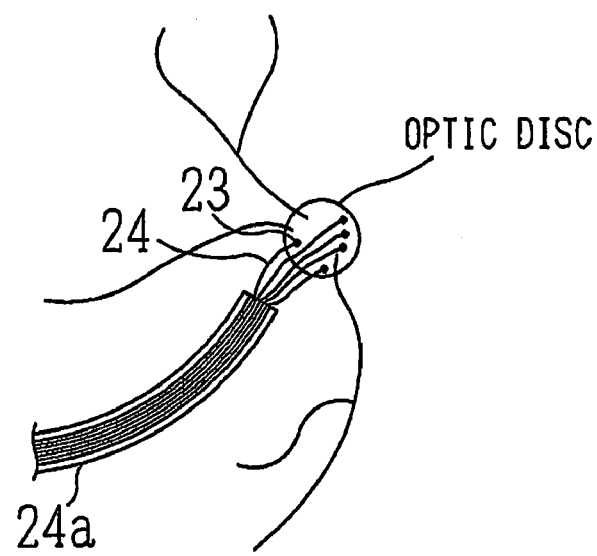

The electrodes 23 are placed (implanted) by sticking them directly into the optic disc at which the nerve fibers that transmit pulse signals from the retinal ganglion cells are concentrated. FIG. 4A and FIG. 4B are views each showing a state in which the electrodes 23 are placed. FIG. 4A is a horizontal cross section of the entire eyeball, and FIG. 4B is an enlarged view of the periphery of the optic disc. The tube 23a into which the lead wires 24 are consolidated is inserted into the eyeball through a pore opened in the sclera, and, is then inserted along the retina as far as the vicinity of the optic disc. Next, the electrodes 23 connected to the distal ends of the lead wires 24 exposed from the distal end of the tube 24a are stuck into the optic disc so that the distal ends of the electrodes 23 are positioned at a point at which direct contact with the blood vessels of the optic disc can be avoided. An indifferent electrode (not shown) is placed (implanted) in the eyeball (in the vitreous body).

An operation for regenerating vision will next be described.

The device 1 is intended to produce the vision by causing phosphenes to generate in the visual field of the patient by outputting the stimulation signals from the electrodes 23 placed in the optic disc. By way of advance preparation, therefore, in a state in which the internal device 20 has been placed in the patient, with use of the setting section 103, the generation positions and the shapes of the phosphenes specific to the patient are varied in relation to a variety of the stimulation conditions and are verified. First, the electrode specifying section 103a makes a setting as to whether to output the stimulation signal from one electrode 23, or whether to output the stimulation signals from a plurality of electrodes 23 at the same time. Further, in the event of simultaneous outputs being made from a plurality of electrodes 23, a combination of the electrodes 23 is set for outputting the stimulation signals at the same time. In the present embodiment, "simultaneous outputs from a plurality of electrodes" may include circumstances where the stimulation signals are output at entirely identical timings, and circumstances where the stimulation signals are output at minuscule intervals over a very short period of time.

Next, the output conditions for the stimulation signal (stimulation condition) are set by the stimulation condition-setting section 103c. The setting section 103c is capable of setting individual parameters such as a current, a frequency, a pulse width, a pulse count, an inter-pulse pause time (an interpulse), a pulse waveform (a single-phase wave or a double-phase wave), and a charge. The settings are displayed on the display 103a. When the pulse waveform is set to the double-phase wave, the wave can be set to a symmetrical double-phase rectangular wave or an asymmetrical double-phase rectangular wave. Moreover, when the pulse wave is set to the asymmetrical double-phase rectangular wave, for example, a pulse level (a current) and a pulse width of the following anodic wave form condition is lowered and broadened in relation to the cathodic waveform condition, thereby achieving a well-balanced state.

Figure 5:
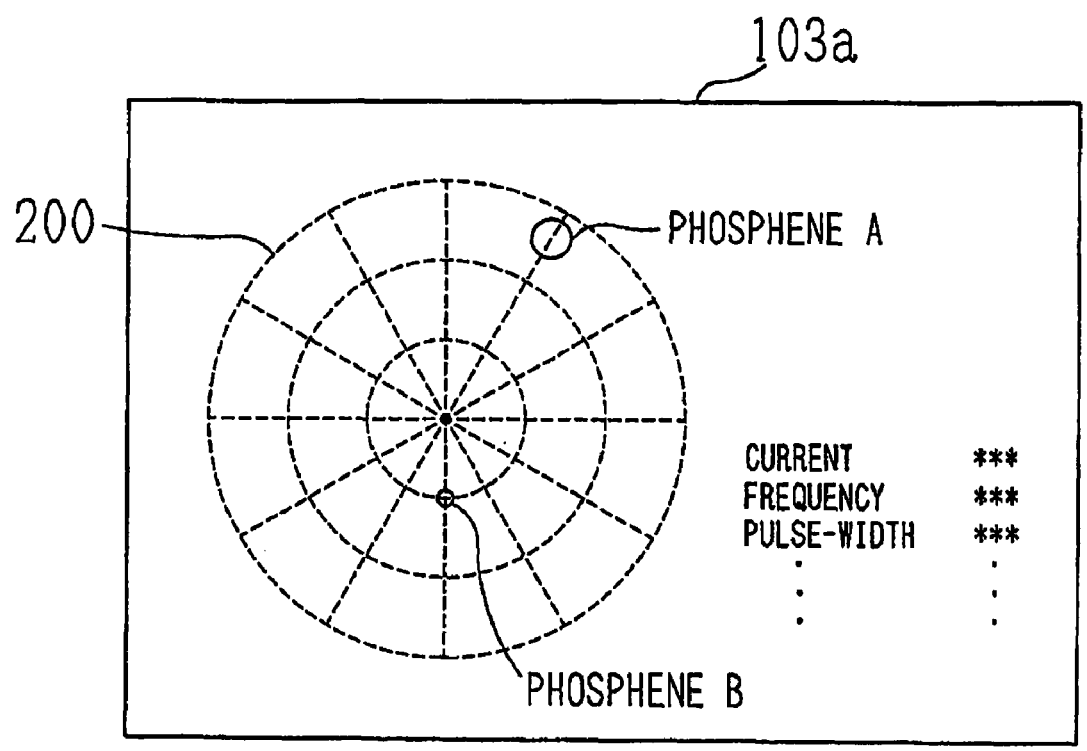
FIG. 5 is a view of an example of displaying positions at which phosphenes have generated on a chart and recording the generation positions.

Next, by a stimulation start button (not shown), the stimulation signals are output from the electrodes 23 under the stimulation conditions that have been set. Then, a confirmation is made as to at which positions in the visual field of the patient, and in what shapes (in what sizes), the phosphenes have generated. As shown in FIG. 5, on the display 103a, a chart 200 can be displayed for recording the generation positions and the shapes of the phosphenes, and the generation positions and the shapes of the phosphenes can be recorded on the chart 200.

For example, in a case where the patient states that the phosphene, at its generation position "has been observed in the size of a coin, outside of a 1 o'clock direction from the center of the visual field", a phosphene mark A is displayed at a position on the chart 200 that is considered appropriate. Furthermore, in circumstances where the stimulation conditions have been changed and the stimulation signal has been output, when the patient states that the phosphene, at its generation position, has been "observed in the size of a distal end of a matchstick almost within a 6 o'clock direction from the center of the visual field", a phosphene mark B is displayed at a position on the chart 200 that is considered appropriate.

In this way, the stimulation conditions can be changed, the stimulation signal can be output, and the phosphenes (the phosphene marks) can be mapped on the chart 200 until the generation positions of the phosphenes have been verified over a wide range in the visual field of the patient. Then, if the generation positions over the wide range in the visual field can be verified to an extent anticipated, they are stored (saved) in the storage section 104 by a save button (not shown). In the storage section 104, the generation positions and the shapes of individual phosphenes, and the stimulation conditions corresponding thereto, are stored in association with each other.

After the advance preparations described above have been carried out, the device 1 is operated. The image data on the object obtained by the photography unit 12 is sent to the processing unit 100. The control section 101 sends to the signal converter section 102 the image data that has been sent and the generation positions and the shapes of the phosphenes specific to the patient stored in the storage section 104. On the basis of the image data and the generation positions and the shapes of the phosphenes, the signal converter section 102 extracts the generation positions and the shapes of the phosphenes required for the patient to recognize the image (the object), sets the stimulation conditions associated therewith; and converts the image data into the stimulation signal data based on the set stimulation conditions. Then, the control section 101 transmits to the internal device 20 through the primary coil 14 the stimulation signal data that has been converted by the signal converter section 102.

The processing control section 22 receives the stimulation signal data sent by the external device 10 (the primary coil 14) through the secondary coil 21, converts it into the stimulation signals, and then outputs it from the electrodes 23. The stimulation signals output from the electrodes 23 stimulates the brain from the optic disc through the optic nerves. In this manner, the patient obtains the vision by recognizing the phosphenes that have generated within the visual field of the patient. In consequence, according to the device of this embodiment, application of electric stimulation from the optic disc, at which the nerve fibers are concentrated, facilitates generation of the phosphenes over a wide range within the visual field, and, as a result, the patient becomes capable of obtaining the vision over the wide range.

Examples of evaluations are shown relating to generation of phosphenes caused by a stimulation signal output from an electrode placed in an optic disc. In these evaluations, how phosphenes generate in the visual field of an examinee was recorded by employing, as the examinee, a patient who was losing vision as a result of pigmentary retinal degeneration; by sticking electrodes so as to place them at predetermined distances at arbitrary positions in the optic disc; and by then outputting the stimulation signals from the electrodes thus placed.

<Examinee>

The examinee was an adult male (his right eye). As electrodes, three platinum wires of 50 microns in diameter were placed at the arbitrary positions in the optic disc. In addition, as an indifferent electrode, one platinum wire of 80 microns in diameter was placed in the vitreous body. The electrodes thus placed have been defined as electrodes "a", "b", and "c".

<Evaluation 1>

Stimulation signals were output one by one from the electrodes "a", "b", and "c" placed in the examinee, and an evaluation, it was made as to ways in which changes in generation positions of phosphenes occur. Output conditions for the stimulation signals (stimulation conditions) were set as follows. A current of 70 µA, a frequency of 40 Hz, and a pulse width of 250 µs were set as fixed values. In addition, a wave form was set as a double-phase wave (more specifically, an asymmetrical double-phase rectangular wave); the following anodic waveform condition relative to the cathodic waveform condition (the current 70 µA and the pulse width 250 µs) was set in such a way that the current was ⅕ and the pulse width× 5. Seven stimulation signals were output from the electrode "a", and two stimulation signals were output from each of the electrodes "b" and "c". Then, every time that the stimulation signals were output, an hearing test was conducted on the examinee so as to establish at what position in the visual field a phosphene had generated. Mapping was then carried out, and the results are shown in FIG. 6.

Figure 6:
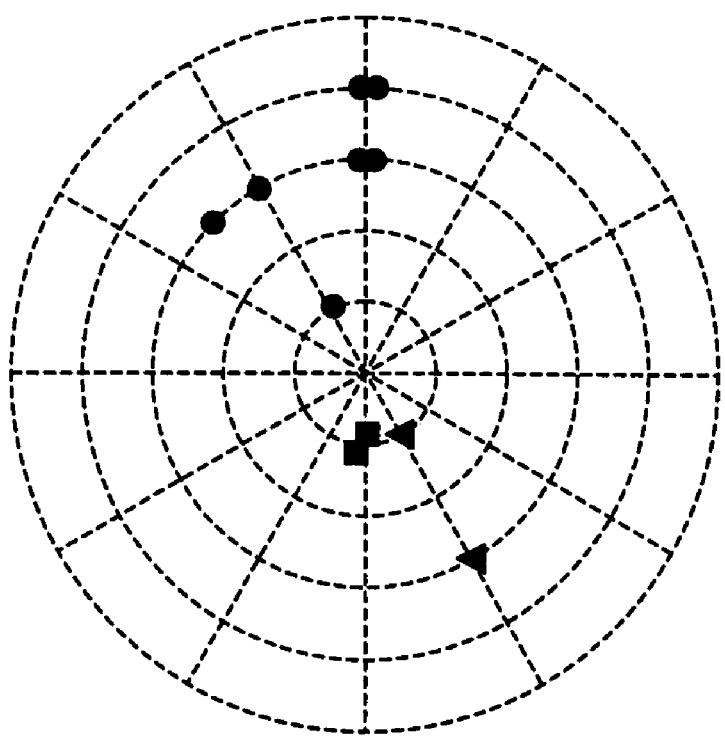
FIG. 6 is a view of a change in generation positions of phosphenes, the change being caused by a difference in positions at which electrodes are placed.

From FIG. 6, it is evident that the generation positions of the phosphenes tend to change by changes in the positions at which the electrodes were placed.

<Evaluation 2>

The electrode "a", identical to that used for evaluation 1 was used on its own on the examinee; stimulation conditions were modified and stimulation signals output; and an evaluation was made of ways in which changes in generation positions of phosphenes occur. The stimulation conditions were set as follows. At a frequency of 40 Hz, four types of settings were provided, i.e., a current of 50 µA and a pulse width of 350 µs (two outputs); a current of 70 µA and a pulse width of 250 µs (seven outputs); a current of 100 µA and a pulse width of 180 µs (one output); and a current of 150 µA and a pulse width of 120 µs (two outputs). At a frequency of 20 Hz, two types of settings were provided, i.e., a current of 30 µA and a pulse width of 580 µs (one output) and a current of 70 µA and a pulse width of 250 µs (one output). Then, every time that the stimulation signals were output, a hearing test was conducted on the examinee so as to establish at what position in the visual field a phosphene had generated. Mapping was then carried out. The results are shown in FIG. 7.

From in FIG. 7, it is evident that, in cases where the stimulation signals are output from the same electrode (electrode "a" in this case), the generation positions of the phosphenes tend to change by varying the stimulation conditions.

<Evaluation 3>

Two from among the electrodes "a", "b", and "c" that were identical to those used in evaluation 1 were arbitrarily used in combination on the examinee; stimulation signals were output from both electrodes at the same time, and an evaluation made as to how generation positions of phosphenes change. The stimulation conditions were set as follows. A current of 70 μA, a frequency of 40 Hz, and a pulse width of 250 μs were set as fixed values, and simultaneous outputs from the electrodes "a" and "b" (two outputs), and simultaneous outputs from the electrodes "b" and "c" (three outputs), were provided. Moreover, every time that the stimulation signals were output, a hearing test was carried out on the examinee so as to establish at what position in the visual field a phosphene had generated. Mapping was then carried out. The results are shown in FIG. 8.

From FIG. 8, it is evident that, in cases where the stimulation signals are output from two electrodes at the same time, the generation positions of the phosphenes tend to change by varying the combination of the electrodes.

As is evident from FIG. 6 to FIG. 8 described above, results demonstrated that when the stimulation conditions changed, the generation positions of the phosphenes also changed. It is considered that such changes in generation positions of phosphenes, depending on different stimulation conditions, varies as a result of variety of conditions such as individual patients and the positions at which the electrodes are placed.

What is claimed is:

1. A vision regeneration assisting device for regenerating vision of a patient by stimulating optic nerves of a patient's eye with electrical stimulation pulse signals output from electrodes which are stuck into an optic disc of the patient's eye, comprising:
    an external device; and
    an internal device,
    the external device comprising:
        a photography unit which picks up an image of an object to be recognized by the patient;
        a power unit which supplies electric power to the external device and the internal device;
        a setting unit that individually sets the individual electrode output based upon various temporal output conditions, wherein the output may be applied simultaneously from a combination of electrodes;
        a storage unit which stores generation positions of phosphenes specific to the patient in association with the set temporal output conditions for the stimulation signals that has prompted the generation of the phosphenes, the storage unit storing the generation positions of the phosphenes in association with the set temporal output conditions for the stimulation signals individually output from each of the electrodes and the generation positions of the phosphenes in association with the set temporal output conditions for the stimulation signals simultaneously output from each of various combinations of electrodes; and
        a signal converter unit which processes image data of the object obtained by the photography unit, extracts optimal generation positions of the phosphenes among the stored generation positions based on the processed image data, and determines real output conditions for the stimulation signals based on the temporal output conditions associated with the extracted generation positions;
        a primary coil which transmits stimulation signal data including the real output conditions, and the electric power; and
        an external controller which controls the external device, and
    the internal device comprising:
        a secondary coil which receives the stimulation signal data and the electric power transmitted from the primary coil;
        the electrodes which are formed in a needle shape and configured to be stuck into the optic disc; and
        an internal controller which is configured to be disposed outside the eye and controls the internal device;
        a first lead wire which connects the secondary coil with the internal controller; and
        second lead wires which respectively connect the internal controller with the electrodes, each of the second lead wires having a length long enough to connect the internal controller disposed outside the eye with the electrodes stuck into the optic disc, each tip of the second lead wires on which the electrode is formed being a free end to be stuck into an optional position of the optic disc,
    wherein the internal controller controls the output of the stimulation signals from the electrodes based on the output conditions to make the patient recognize the object by the generation of the phosphenes.

2. The vision regeneration assisting device according to claim 1, wherein the temporal output conditions and the real output conditions include at least one among: a current value, a frequency and a pulse width of the stimulation signals.

* * * * *